(12) United States Patent
Su et al.

(10) Patent No.: US 7,155,959 B2
(45) Date of Patent: Jan. 2, 2007

(54) NANODISK SENSOR AND SENSOR ARRAY

(75) Inventors: Ming Su, Evanston, IL (US); Vinayak P. Dravid, Glenview, IL (US)

(73) Assignee: Northwestern University, Evanston, IL (US)

( * ) Notice: Subject to any disclaimer, the term of this patent is extended or adjusted under 35 U.S.C. 154(b) by 39 days.

(21) Appl. No.: 10/782,720

(22) Filed: Feb. 18, 2004

(65) Prior Publication Data

US 2004/0194535 A1    Oct. 7, 2004

Related U.S. Application Data

(60) Provisional application No. 60/448,636, filed on Feb. 18, 2003.

(51) Int. Cl.
*G01N 7/00* (2006.01)
(52) U.S. Cl. .................................. 73/31.05
(58) Field of Classification Search ............ 73/31.01, 73/31.05, 31.06
See application file for complete search history.

(56) References Cited

U.S. PATENT DOCUMENTS 5,569,561 A * 10/1996 Exnar et al. ............... 429/335
5,773,834 A * 6/1998 Yamamoto et al. ........ 250/423 F
6,555,236 B1 * 4/2003 Nakamura et al. .......... 428/447
6,673,644 B1 * 1/2004 Gole et al. .................... 438/49
6,791,338 B1 * 9/2004 Bratkovski et al. ......... 324/600

FOREIGN PATENT DOCUMENTS

JP            61289549        * 12/1986

* cited by examiner

*Primary Examiner*—Robert Raevis
(74) *Attorney, Agent, or Firm*—Sheridan Ross P.C.

(57) ABSTRACT

The invention provides a sensor array with different nanodisk sensors that may be fabricated by direct site-specific dip-pen nanopatterning (DPN) using precursor inks. The good flow characteristics and strong affinity of the sols to measurement electrodes enable intimate ohmic contact. The measurable, reproducible and proportionate changes in the resistance of the sensors when exposed to trace quantities of oxidative and reducing gases constitute the basis for nanodisk gas sensors. The nanodisk sensors show rapid response and ultra-fast recovery for the detection of nitrogen dioxide and acetic acid vapor. Based on the principles of pattern recognition of the olfactory system, an electronic nose that can "smell" different gaseous species is provided with the multiple nanodisk sensor array. These nanodisk sensors have gas recognition ability, instant response and rapid recovery, compact size and integration with the established microelectronics platform and are well-suited for the on-site and real-time detection of gases.

36 Claims, 4 Drawing Sheets

NANODISK SENSOR AND SENSOR ARRAY

CROSS REFERENCE TO RELATED APPLICATION

This application claims priority under 35 U.S.C. § 119(e) to U.S. Provisional Patent Application Ser. No. 60/448,636 filed on Feb. 18, 2003, which is incorporated herein in its entirety by this reference.

GOVERNMENT RIGHTS

This invention was made in part with government support under National Science Foundation (NSF) Grant No.EEC0118025 and Air Force Office of Scientific Research (AFOSR) Grant No. F49620-02-1-0283. The government has certain rights in this invention.

FIELD OF THE INVENTION

The invention resides in the field of miniature gas and temperature sensors and methods of making the same.

BACKGROUND OF THE INVENTION

Metal oxide semiconductor (MOS) sensors are widely used in controlled combustion, toxic and inflammable gas leakage detection, and temperature measurements. The requirements for the on-site detection of hazardous gases call for integrated sensors with low energy consumption, fast response and rapid recovery. More importantly, the sensor should be able to recognize the type of gas that induces the response, and exhibit rapid sensing and subsequent recovery, thus behaving like a smart "electronic nose." These considerations impose even more stringent requirements for sensor elements and their integration within the established microelectronics platforms. Such smart sensors are essential in numerous industrial, domestic and warfare environments including chemical industries, pollution monitoring, food quality control and chemical weapons detection.

The advent of nanostructured materials exhibiting enhanced and unusual physical and chemical properties, and the means to fabricate or pattern structures at the nanoscale, have paved the way for new and improved biological and chemical sensing and detection. As a result, the fabrication of miniaturized sensors using emerging nanomaterials has been an active topic in sensor research. One-dimensional nanostructured elements such as nanowires (e.g. carbon nanotube, silicon nanowire, semiconductor nanoribbon and mesowire) have been used to detect biological molecules and industrial gases. However, the necessity of separate steps in the synthesis and purification of nanowires and sensor fabrication requires additional manipulation to incorporate nanowires into electronic circuitry. Furthermore, it is very difficult to control the position and orientation of nanowires when using direct deposition techniques to pattern nanowire suspensions onto substrates.

External manipulations using atomic force microscope (AFM) and electrophoresis of nanowires inside a suspension have been used to increase the efficiency of nanowire bridging on electrode gaps. Another improved approach is the use of microfluidics to align a multitude of nanowires at the same time, followed by the deposition of electrodes across the desired nanowires. However, such "reverse" construction approaches require access to expensive and sophisticated facilities for nanowire observation and measurement of electrode deposition, and they are generally time-consuming with questionable batch-to-batch reproducibility. Furthermore, as far as integrated sensor construction is concerned, it remains a formidable challenge for parallel fabrication methods such as microfluidics to create sensor arrays with multiple detection capability using different sensor materials.

Thus, there exists a need for an effective and efficient approach for the nanopatterning of nanoporous sensor materials, and the subsequent fabrication of gas-sensing miniaturized nanodisk sensors.

SUMMARY OF THE INVENTION

The present invention provides a sensor for temperature and gas detection comprising a sol gel nanodisk fabricated between conducting electrodes. The sol gel nanodisk is a semi-crystallized structure having surface oxygen ions and the electrodes are any conducting material, preferably a metal. The sensor is fabricated on an insulating substrate and the sol gel nanodisk preferably has a width of about 4 μM and a length of about 5 μM. The sensor may be composed of many sol gel nanodisks fabricated between conducting electrodes on a single substrate.

Another embodiment of the present invention provides a method of fabricating a nanodisk sensor including contacting a reservoir of a sol gel with a tip and contacting the tip between electrodes on a surface to deposit a sol gel nanodisk in ohmic contact with the electrodes. The process is based on dip pen nanolithography and the tip used may be a microcantilever tip. The electrodes may be formed by photolithography and electron bean deposition on a surface prior to contacting the tip.

Another embodiment of the present invention provides a sensor for temperature and gas detection fabricated by a method including contacting a reservoir of a sol gel with a tip and contacting the tip between two electrodes on a surface to deposit a sol gel nanodisk in ohmic contact with the electrodes.

Another embodiment of the present invention provides a method of detecting an ambient chemical by exposing a sensor to at least one ambient chemical wherein the sensor is a sol gel nanodisk fabricated between conducting electrodes. Preferably, conductance between the electrodes following exposure of the sensor occurs in less than about 200 seconds and the conductance between the electrodes following exposure of the sensor recovers in less than about 400 seconds.

DETAILED DESCRIPTION OF THE INVENTION

The present invention provides nanodisk sensors composed of an inorganic nanosensor element placed between measurement electrodes for proper signal transduction and detection and an efficient and effective method of fabricating the sensors by a modified dip-pen nanopatterning (DPN) approach.

The nanodisk sensors of the present invention are fabricated on a suitable insulating surface such as a silicon wafer having a silicon dioxide covering. As shown in FIG. 1C, the sensor is a nanodisk composed of a sol gel chemical aligned between two measurement electrodes. The sol gel material shows variable conductivity based on exposure to and reaction with different ambient chemicals. The resistance across these sensors can be measured and reproducibly increases and decreases after exposure of the nanodisk to different chemicals or exposure to different temperatures. Therefore, by choosing the sol gel material composing the nanodisk and monitoring the resistance across the sensor, the presence of a specific chemical in the presence of the sensor can be rapidly and reproducibly detected. Additionally, many different sensors can be fabricated on a single wafer, each composed of a different sol gel material. If the resistance of each sensor is monitored following exposure to different chemicals, a pattern of responses from each sensor can be collected. These patterns will be unique to many chemicals and, following exposure to these chemicals or combinations of chemicals, the pattern of sensor responses can be compared to known chemical response patterns to detect and identify the presence of specific ambient chemicals in the vicinity of the sensor.

Figure 1:
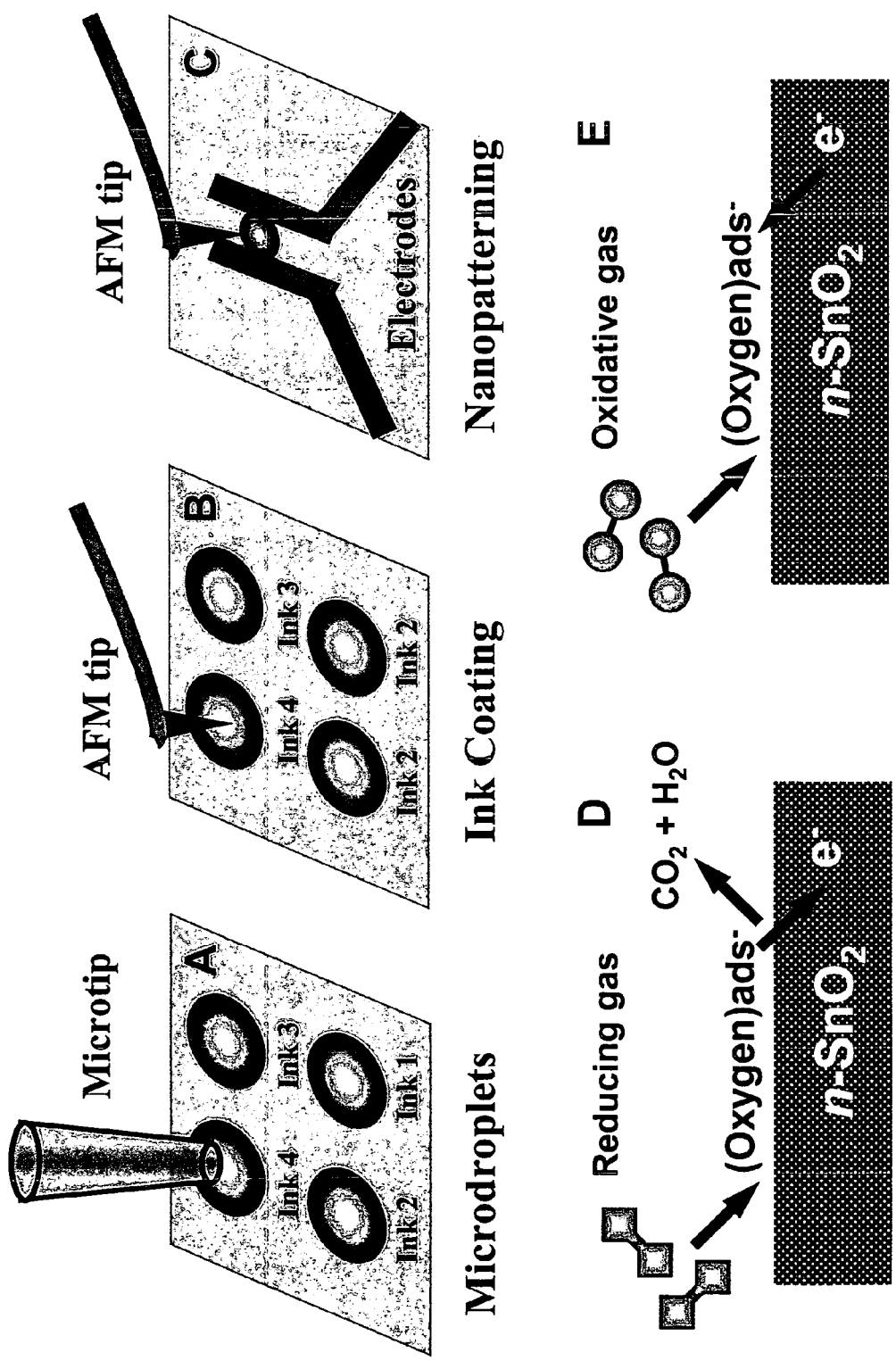
FIG. 1 (A, B and C) is a schematic representation of the dip-pen nanopatterning process of the present invention. The reactions between gaseous molecules with surface adsorbed oxygen ions change the resistance of $SnO_2$ semiconductor sensors (D and E).
Figure 3:
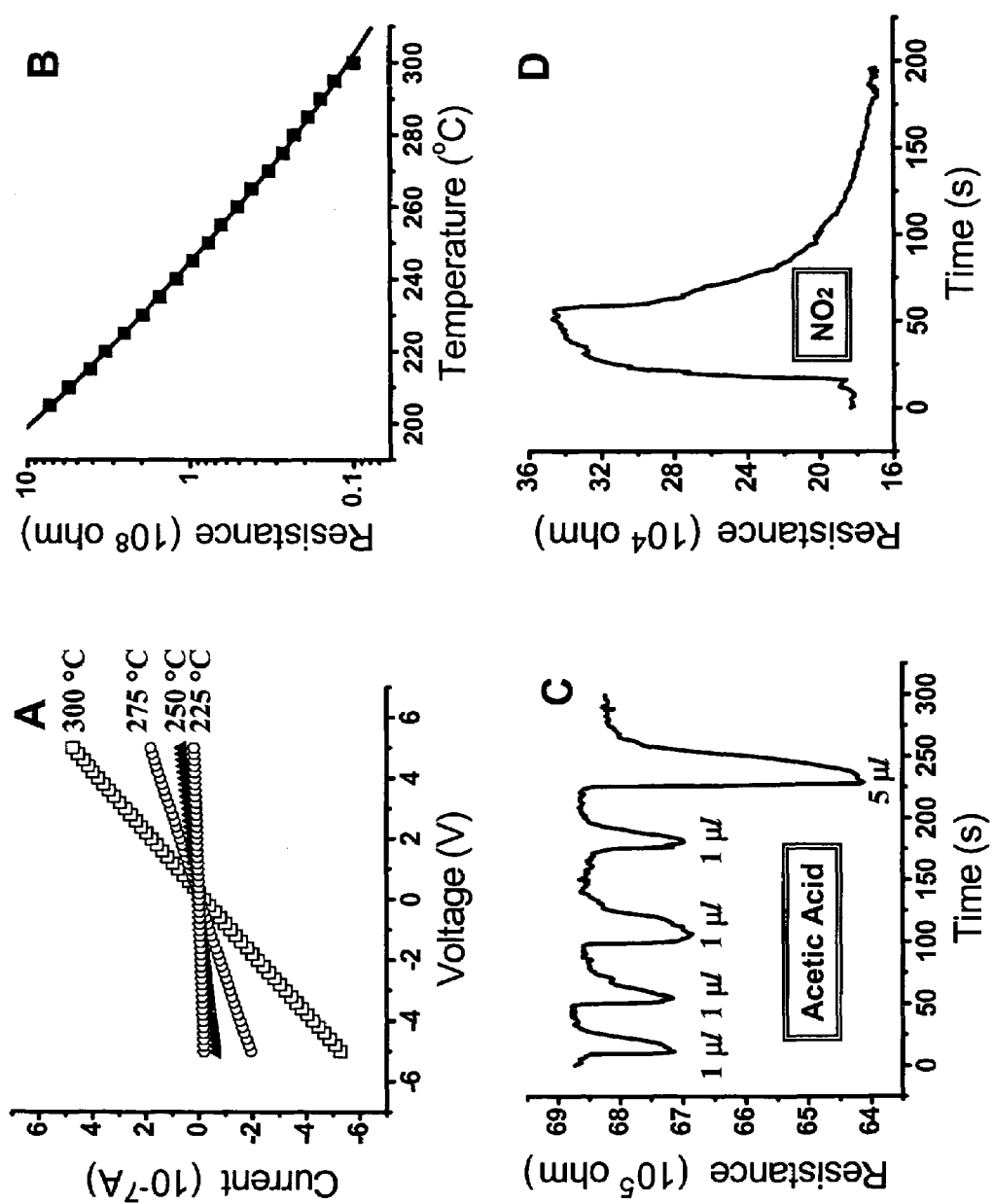
FIG. 3 (A) shows the I-V curves of a nanodisk $SnO_2$ sensor at different temperatures; (B) shows the resistance change of the nanodisk sensor in the temperature range between 200° C. and 300° C.; (C) shows the sensing response of a nanodisk $SnO_2$ to different concentrations of acetic acid vapor introduced by injecting liquid chemical into the chamber at about 280° C. (air as the balance gas). The acetic acid concentration is estimated based on the chamber volume (about 300 ml) and the flow rate of air (approximately 2500 ml/min). The response and recovery is consistent and repetitive; (D) is an expanded view of the response of a nanodisk $SnO_2$ sensor of the present invention exposed to about 200 ppm $NO_2$ at about 300° C. (air as the balance gas) showing the rapid response to gas exposure and quick recovery to the original resistance value.

The sol gel materials suitable for use as nanodisk sensors in the present invention are semi-crystallized structures rich in surface oxygen ions that determine the resistance of the semiconductor nanodisks. Examples include ionic surfactants, nonionic surfactants polymers and hybrid surfactants. Preferred examples include $SnO_2$, Ti—$SnO_2$, Co—$SnO_2$, Ni—$SnO_2$, Cu—$SnO_2$, Zn—$SnO_2$, Cd—$SnO_2$, Pt—$SnO_2$, $TiO_2$, $ZrO_2$, ZnO, MgO, CaO, $Li_2O$, $B_2O_3$, CO, $CO_2$, $SiO_2$, $GeO_2$, $N_2O$, NO, $N_2O_3$, $NO_2$, $N_2O5$, $SO_2$, $SO_3$, $SeO_2$, $SeO_3$, $TeO_2$, $TeO_3$, $Cl_2O$, $ClO_2$, $Cl_2O_7$, $Br_2O$, $BrO_2$, $I_2O_5$ and $I_2O_7$. Thermal desorption of oxygen ions with the nanodisk reduces the resistance of such sensors. The surface reactions between adsorbed oxygen ions and reducing gases remove some oxygen ions and release electrons that contribute to the conduction. Alternatively, oxidative gases lead to an increase in resistance by increasing the concentration of surface adsorbed oxygen ions as depicted in FIG. 1(D and E). A stable ohmic contact between the sensor and electrodes is therefore imperative to obtain reliable sensor response, as non-ohmic effects often mask the normal response of the sensor. The nominal resistance of $SnO_2$ nanodisk sensors at 300° C. varies from several MΩ to hundreds of MΩ. FIG. 3A shows the current (I) versus voltage (V) curves of one $SnO_2$ nanodisk measured in pure air from 200° C. to 300° C. The linear I-V curves at different temperatures shown in FIG. 3A indicate appropriate ohmic contact between the nanodisk and electrodes.

As shown in FIG. 3B, the resistance decreases continuously as temperature is increased. Thus another embodiment of the present invention is a semiconductor nanodisk thermistor. The good flowability and the strong affinity of the sol inks to the substrate and electrodes are a key to this intimate contact. In contrast, nanowire-based nanosensors often exhibit non-ohmic contact behavior owing to the complicated and variable nature of the contact surfaces.

The response and recovery times of the nanodisk sensors of the present invention are much shorter than the corresponding times for conventional Cd-doped high performance $SnO_2$ sensors. Although semiconducting carbon nanotubes exhibit even shorter response times (about 2–10 seconds), nanotubes require a much longer recovery time (approximately 12 hours at room temperature and about 1 hour at 200° C.) and are therefore impractical as gas sensors requiring repeatable detection with equal sensitivity and response characteristics.

Figure 2:
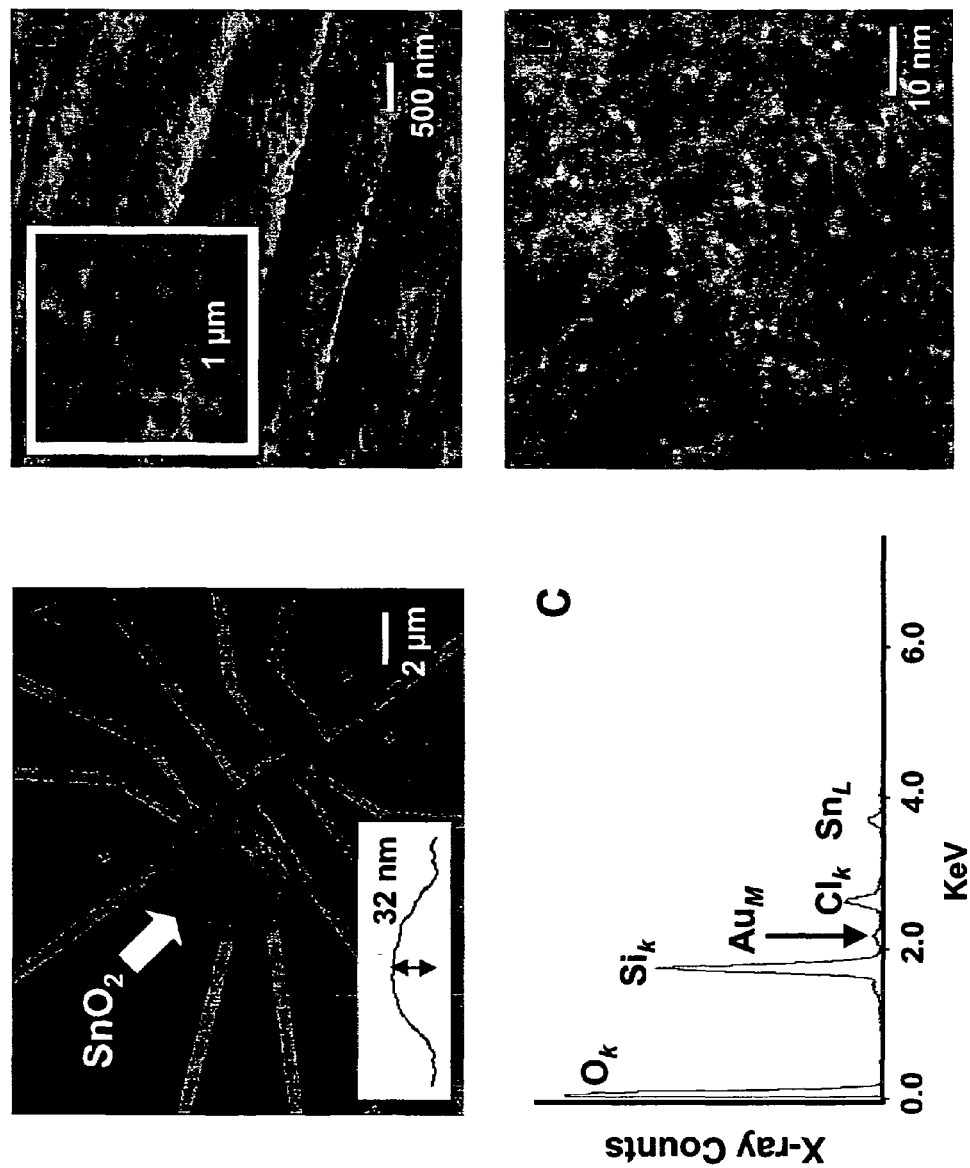
FIG. 2 (A) is an SEM image of a nanodisk $SnO_2$ sensor that is trapped between pre-fabricated transport measurement electrodes; (B) is an AFM image of a spin-coated thin film of $SnO_2$ showing the existence of many nanochannels with diameters of about 10–100 nm; (C) shows the x-ray microanalysis (EDS) spectrum collected by focusing the electron beam on the nanodisk, indicating the presence of appropriate sensor chemical species; (D) is a TEM image of a similar bulk form of a $SnO_2$ sample after heat-treatment, showing the nanoporous structure.

The rapid response and ultra-fast recovery of nanodisk sensors are believed to be due to their miniature sizes and well-developed open-channel nanostructures. The nanochannels or nanopores present in the nanodisk sensors (FIG. 2(B and D)) facilitate the diffusion of gases, permitting intimate and rapid contact with the active sensor surfaces. The performance of the nanodisk sensors of the present invention is invariant even after storage under ambient conditions for several months, indicating their robust nature. It is possible to vary the sensor sensitivity using different high melting point metals as electrodes that enable higher annealing and working temperatures, as well as optimization of overall composition, including type and extent of dopant concentration.

Normally MOS sensors cannot fully discriminate different gaseous species. The selectivity to certain gas is optimized by modulating the composition of the nanodisk sensors (e.g. with promoters), adjusting the microstructure of the sensor elements, and modifying the sensing conditions. The addition of catalytic additives is frequently used to enhance sensor selectivity. While a definitive discrimination of one gas from another is usually not feasible, especially when such gases show similar interactions with sensors, it is possible to minimize, if not circumvent, the need for high specificity and selectivity sensors to recognize different gases by creating a collective reference response to a multitude of gases via an array of diverse sensor elements.

Figure 4:
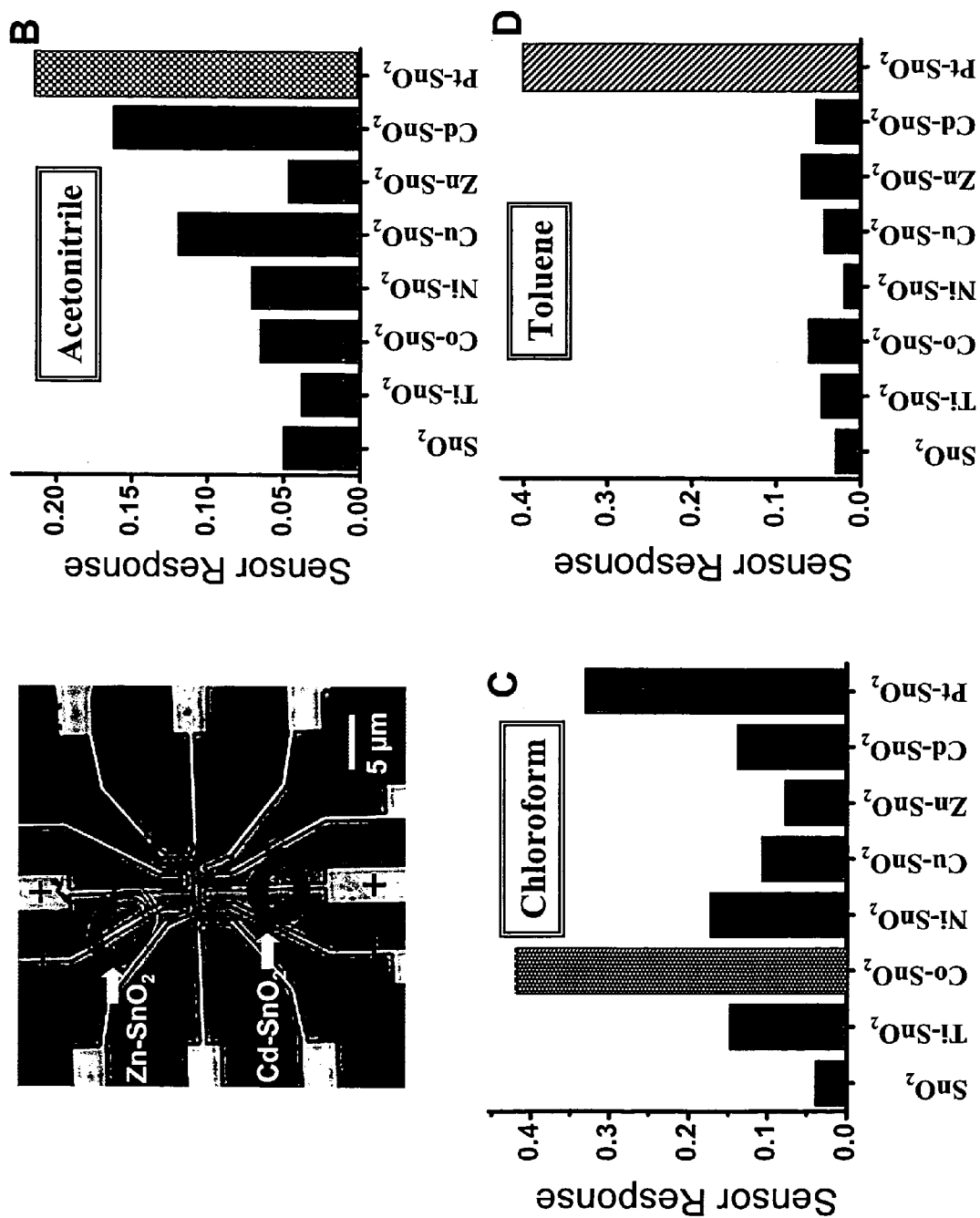
FIG. 4 (A) is an optical microscope image of two nanodisk sensors (Zn—$SnO_2$, Cd—$SnO_2$) of the nanodisk array integrated on a single electronic chip. The response of each gas-sensor combination is collected at 300° C. after injection of 5 μl liquid chemical into the chamber (300 ml) at a pure air flow rate of 2500 ml/min. The characteristic response patterns for acetonitrile (B), chloroform (C) and toluene (D) of the array are shown as a sequence of sensor compositions: $SnO_2$, Ti—$SnO_2$, Co—$SnO_2$, Ni—$SnO_2$, Cu—$SnO_2$, Zn—$SnO_2$, Cd—$SnO_2$ and Pt—$SnO_2$. The data in the Y-axis are the ratios of the resistance changes to the resistances before introducing the organic vapors (chloroform reduces the resistance of all eight sensors).

Thus, in a preferred embodiment of the present invention, a diverse array of nanodisk sensors is constructed on a single electronic chip. In one embodiment the array of sensors consists of eight different nanodisk sensors including nominally pure $SnO_2$ and its doped versions including $Ti$—$SnO_2$, $Co$—$SnO_2$, $Ni$—$SnO_2$, $Cu$—$SnO_2$, $Zn$—$SnO_2$, $Cd$—$SnO_2$ and $Pt$—$SnO_2$, with the molar ratios of metal additives to tin kept at about 0.05. FIG. 4A shows an optical microscope image of two separate sensor elements in the array. FIG. 4(B–D) shows the response of these sensors of the array to three organic vapors (chloroform, acetonitrile and toluene) measured at 300° C. using pure air as the balance gas. These chemical vapors approximately simulate the gases that can be used as chemical weapons (e.g. sarin). The sensor response to a given vapor is not the same due to the different reactivity of the gas on the specific sensor: $Pt$—$SnO_2$ shows the largest response to acetonitrile and toluene, while $Co$—$SnO_2$ is more sensitive to choroform. The resistance of the eight sensors reduces upon exposure to chloroform, and increases upon exposure to acetonitrile and toluene. Such diversity in response is helpful to find the characteristic patterns of the sensor array to each gas through a proper pattern recognition process. Based on the response patterns of each gas, the discrimination of specific gas is possible using the principle similar to that of an olfactory system wherein a small number of non-selective receptors allow for the discrimination of over a thousand different odors. Such "digital smell" patterns can be stored for future reference to warn of the presence of specific gaseous species in the vicinity of the sensor array. Thus, the array of nanodisk sensors constitutes a digital electronic nano-nose for on-site real-time detection of hazardous gas species.

Dip pen nanolithography/nanopatterning (DPN) is based on the controlled transfer of molecular ink from an ink-coated microtip to a substrate. The two unique features of DPN are its highly localized patterning capability and the serial nature of its operation, which enable successive patterning of different inks onto specific locations. In principle, DPN can be used to pattern many materials on various substrates if there is a driving force for moving the ink from the tip to the substrate, and a reasonable affinity of the ink to the substrate.

Practically however, DPN experiments are limited by factors such as the solubility of the desired ink, the transfer and stability of the material, and the adsorption of the materials on the substrate. Thus, the ink selection is essential to the success of DPN experiments. In the present invention, sol-gel sensor materials provide a wide variety of choices for suitable inks because the sol-gels are chemically versatile with relatively inexpensive precursors which are amenable to handling in liquid form. Thus, a multitude of solid-state structures including sensors, active catalysts and support systems can be prepared using the sol-gel method.

To fabricate the nanodisk sensors of the present invention, an improved ink coating and patterning method was developed for DPN. As depicted in FIG. 1, the method combines the operations of micro-pen patterning and traditional DPN provides more control and flexibility over previous ink coatings and patterning methodologies. In this method, droplets of sol gel are deposited on a suitable insulating substrate to form ink reservoirs at millimeter dimension (microdeposition). Use of sol-based precursors permits direct nanopatterning of a wide range of inorganic and hybrid sensor elements, invoking the site- and shape-specificity of DPN combined with the versatility of sol-gel method. The top plane of the reservoir is touched with a tip (ink transfer). The amount of adsorbed liquid can be adjusted by varying the holding time and dip-in depth. Further adjustment can be achieved by touching the coated tip to a liquid-free area on the substrate. The liquid-coated AFM tip is then used for nanopatterning (nanodeposition) of the liquid onto the insulating substrate wafer between the pre-fabricated measurement electrodes in a manner similar to regular DPN onto appropriate substrates.

The sol gel liquid for deposition on the insulating substrate is prepared by dissolving 1 g of block copolymer poly(ethyleneoxide)-b-poly(propyleneoxide)-b-poly(ethyleneoxide) ($EO_{20}PO_{70}EO_{20}$)(Pluronic P123, BASF) and 0.01 mol tin chloride in 10 g ethanol. The ethanol-solvable salts of metals (titanium, cobalt, nickel, copper, zinc, cadmium, platinum) are added separately to the tin chloride sol to prepare a series of sol liquids. The molar ratios of the sensing promoters to tin are controlled to about 0.05 which is consistent with reasonable dopant levels found in conventional sensors. The as-prepared sols have excellent flow characteristics and are optically translucent with colors dependent upon the nature of the metal ions. An AFM is used under ambient conditions to pattern the nanodisk sensors precisely between the electrodes on the substrate. For example, in a preferred embodiment, a ThermoMicroscope AFM and silicon nitride microcantilevers (force constant of about 0.05 N/m) are used in the DPN under ambient conditions with a tip-surface contact force of about 0.5 nN. In this embodiment, a 90 µm scanner with closed loop scan control is used to minimize the piezo tube drift. The ethanol solvent slows the hydrolysis of the liquids compared to water, and the gelation process occurs after several hours, allowing sufficient time for DPN patterning. The polymer surfactant stabilized tin ink hydrolyzes to form mesoporous structures after DPN patterning. The 1 electrodes (about 20 nm thick metal, on top of an approximately 5 nm chromium buffer layer) are prepared by photolithography and electron beam deposition on silicon (100) substrates that are covered with about 600 nm silicon dioxide. The sensors are annealed at about 320° C. in air for about 5–10 hours. After wiring out via a chip carrier, the sensor assembly is then mounted for evaluation and the transport properties are monitored by a Keithley 2400 source meter at applied voltage of about 5 V.

The serial process of DPN is effectively exploited to pattern an array of diverse nanosensor elements to enhance the selectivity and specificity for gas detection. This not only allows the construction of a combinatorial inorganic (doped or hybrid) nanostructure array in search for proper sensor response, but also paves the way for the construction of an on-chip "smart electronic nano-nose" capable of discriminating a wide variety of gases with the collective reference response from all the nanosensor elements.

FIG. 2A shows a scanning electron microscope (SEM) image of a $SnO_2$ nanodisk patterned between electrodes by holding an ink-coated tip at the location for approximately 30 seconds. The length and width of the nanodisk are approximately 5 nm and 4 nm, respectively, while the height is about 32 nm at the center (see AFM image, FIG. 2A, inset). On a spin-coated film (using the same sol), AFM imaging indicates many open nanoscale channels (with diameters of about 10–100 nm) normal to the z-axis of the film (FIG. 2B). The composition of the nanodisk can be confirmed by energy dispersive X-ray (EDX), which shows expected peaks of tin, silicon, gold, oxygen and residual chloride (FIG. 2C). A transmission electron microscope (TEM) image collected on a similarly prepared bulk $SnO_2$ sample shows the presence of nanopores encompassed by sidewalls (FIG. 2D).

EXAMPLES

Example 1

This example demonstrates the rapid response and recovery time characteristics of sensors of the present invention. The sensing performance of two $SnO_2$ nanodisk sensors was probed by using acetic acid vapor and nitrogen dioxide ($NO_2$) as model gases. Injection of about 1 µl acetic acid into an approximately 300 ml chamber at about 280° C. (the flow rate of the balance gas air was approximately 2500 ml/min) reduced the sensor resistance compared to that in pure air. Injection of about 5 µl acetic acid led to a proportionately larger change in resistance. The sensor worked effectively after each injection of acetic acid in repeated cycles (FIG. 3C). For about 1 µl acetic acid (the equivalent concentration is estimated to be about 330 ppm), the sensor resistance reached minimum in 5 seconds, and recovered to its original value in about 20 seconds. As a comparison, conventional thin film $SnO_2$ sensors show a response time of about 200 seconds and a recovery time of about 700 seconds to about 500 ppm acetic acid vapor at about 280° C. Exposure to $NO_2$ increased the resistance of nanodisk $SnO_2$ sensors compared to resistance in air (FIG. 3D). The response and recovery time of the nanodisk sensor to about 200 ppm $NO_2$ at about 300° C. was about 20 seconds and about 65 seconds respectively. These times are much shorter than the corresponding times for conventional Cd-doped high performance $SnO_2$ sensors operated at about 250° C., for the detection of about 100 ppm $NO_2$ (which are approximately 50 seconds and 480 seconds, respectively). Although semiconducting carbon nanotubes exhibit even shorter response times (approximately 2–10 seconds), nanotubes need much longer recovery times (approximately 12 hours at room temperature and 1 hour at 200° C).

Example 2

This example demonstrates the response of a nanodisk sensor array of the present invention exposed to a combination of gases with the compilation of a response profile for the gas mixture. FIG. 4A shows an optical microscope image of two separate sensor elements in the array. The response of each sensor of the array to three organic vapors (chloroform, acetonitrile and toluene) was measured at 300° C. using pure air as the balance gas. An approximately 5 µl liquid droplet of each chemical was injected into an approximately 300 ml chamber to produce a contaminated environment at the air flow rate of about 2500 ml/min. The relative resistance change (Rg–Ra)/Ra, of each gas-sensor pair, where Ra and Rg are the resistances before and after introducing vapor, was plotted against the type of additive.

What is claimed is:

1. A sensor for temperature and gas detection comprising a sol gel nanodisk fabricated between conducting electrodes whereby the sol gel nanodisk comprises a semi-crystallized structure having surface oxygen ions.

2. The sensor of claim 1, wherein the semi-crystallized structure comprises an inorganic molecule selected from the group consisting of $SnO_2$, Ti—$SnO_2$, Co—$SnO_2$, Ni—$SnO_2$, Cu—$SnO_2$, Zn—$SnO_2$, Cd—$SnO_2$, Pt—$SnO_2$, $TiO_2$, $ZrO_2$, ZnO, MgO, CaO, $Li_2O$, $B_2O_3$, CO, $CO_2$, $SiO_2$, $GeO_2$, $N_2O$, NO, $N_2O_3$, $NO_2$, $N_2O5$, $SO_2$, $SO_3$, $SeO_2$, $SeO_3$, $TeO_2$, $TeO_3$, $Cl_2O$, $ClO_2$, $Cl_2O_7$, $Br_2O$, $BrO_2$, $I_2O_5$ and $I_2O_7$.

3. The sensor of claim 1, wherein the conducting electrodes are comprised of a metal.

4. The sensor of claim 1, wherein the sensor is fabricated on an insulating substrate.

5. The sensor of claim 1, wherein the sol gel nanodisk has a width of about 4 µM and a length of about 5 µM.

6. The sensor of claim 1, wherein the sol gel nanodisk comprises an ionic surfactant.

7. The sensor of claim 1, wherein the sol gel nanodisk comprises a nonionic surfactant.

8. The sensor of claim 1, wherein the sol gel nanodisk comprises poly(ethyleneoxide)-b-poly(propyleneoxide)-b-poly(ethyleneoxide) copolymer.

9. A chemical sensor comprising at least two sol gel nanodisks fabricated between conducting electrodes on a single substrate.

10. A method of fabricating a nanodisk sensor comprising,
   a. contacting a reservoir of a sol gel with a tip; and,
   b. contacting the tip between electrodes on a surface to deposit a sol gel nanodisk in ohmic contact with the electrodes.

11. The method of claim 10, comprising the additional step of contacting a second surface with the tip after contacting the reservoir of a sol gel and before contacting the surface between the electrodes.

12. The method of claim 10, wherein the sol gel nanodisk comprises a compound selected from the group consisting of surfactant, solvent, metal and combinations thereof.

13. The method of claim 10, wherein the sol gel nanodisk comprises copolymer poly(ethyleneoxide)-b-poly(propyleneoxide)-b-poly(ethyleneoxide), ethanol and tin chloride.

14. The method of claim 13, wherein the sol gel nanodisk additionally comprises the ethanol-solvable salt of a metal selected from the group consisting of titanium, cobalt, nickel, copper, zinc, cadmium and platinum.

15. The method of claim 10, wherein the tip is a microcantilever.

16. The method of claim 10, comprising the additional step of fabricating the electrodes by photolithography and electron bean deposition on a surface prior to contacting the tip.

17. A sensor for temperature and gas detection fabricated by a method comprising,
   a. contacting a reservoir of a sol gel with a tip; and,
   b. contacting the tip between electrodes on a surface to deposit a sol gel nanodisk in ohmic contact with the electrodes.

18. The sensor of claim 17, wherein the sol gel comprises a tin dioxide selected from the group consisting of $SnO_2$, Ti—$SnO_2$, CO—$SnO_2$, Ni—$SnO_2$, Cu—$SnO_2$, Zn—$SnO_2$, Cd—$SnO_2$, Pt—$SnO_2$, $TiO_2$, $ZrO_2$, ZnO, MgO, CaO, $Li_2O$, $B_2O_3$, CO, $CO_2$, $SiO_2$, $GeO_2$, $N_2O$, NO, $N_2O_3$, $NO_2$, $N_2O5$, $SO_2$, $SO_3$, $SeO_2$, $SeO_3$, $TeO_2$, $TeO_3$, $Cl_2O$, $ClO_2$, $Cl_2O_7$, $Br_2O$, $BrO_2$, $I_2O_5$ and $I_2O_7$.

19. The sensor of claim 17, wherein the electrodes are comprised of a metal.

20. The sensor of claim 17, wherein the surface comprises an insulating substrate.

21. The sensor of claim 17, wherein the sol gel comprises poly(ethyleneoxide)-b-poly(propyleneoxide)-b-poly(ethyleneoxide) copolymer.

22. The sensor of claim 17, wherein the sol gel nanodisk comprises copolymer poly(ethyleneoxide)-b-poly(propyleneoxide)-b-poly(ethyleneoxide), ethanol and tin chloride.

23. The sensor of claim 17, wherein the tip is a microcantilever.

24. The sensor of claim 17, comprising the additional step of fabricating the electrodes by photolithography and electron bean deposition on a surface prior to contacting the tip.

25. A method of detecting an ambient chemical comprising exposing a sensor to at least one ambient chemical wherein the sensor comprises a sol gel nanodisk fabricated between conducting electrodes.

26. The method of claim 25, wherein the sol gel nanodisk comprises a tin dioxide selected from the group consisting of $SnO_2$, Ti—$SnO_2$, Co—$SnO_2$, Ni—$SnO_2$, Cu—$SnO_2$, Zn—$SnO_2$, Cd—$SnO_2$, Pt—$SnO_2$, $TiO_2$, $ZrO_2$, ZnO, MgO, CaO, $Li_2O$, $B_2O_3$, CO, $CO_2$, $SiO_2$, $GeO_2$, $N_2O$, NO, $N_2O_3$, $NO_2$, $N_2O5$, $SO_2$, $SO_3$, $SeO_2$, $SeO_3$, $TeO_2$, $TeO_3$, $Cl_2O$, $ClO_2$, $Cl_2O_7$, $Br_2O$, $BrO_2$, $I_2O_5$ and $I_2O_7$.

27. The method of claim 25, wherein the conducting electrodes are comprised of metal.

28. The method of claim 25, wherein the sensor is fabricated on an insulating substrate.

29. The method of claim 25, wherein the sol gel nanodisk has a width of about 4 μM and a length of about 5 μM.

30. The method of claim 25, wherein the sol gel nanodisk comprises poly(ethyleneoxide)-b-poly(propyleneoxide)-b-poly(ethyleneoxide) copolymer.

31. The method of claim 25, wherein conductance between the electrodes following exposure of the sensor occurs in less than about 200 seconds.

32. The method of claim 25, wherein the conductance between the electrodes following exposure of the sensor occurs in less than about 10 seconds.

33. The method of claim 25, wherein the conductance between the electrodes following exposure of the sensor recovers in less than about 400 seconds.

34. The method of claim 25, wherein the conductance between the electrodes following exposure of the sensor recovers in less than about 30 seconds.

35. A sensor comprising a sol gel nanodisk in direct ohmic contact with at least two conducting electrodes, wherein the sol gel nanodisk comprises a semi-crystallized structure having surface oxygen ions.

36. The sensor of claim 35, wherein the semi-crystallized structure comprises an inorganic molecule selected from the group consisting of $SnO_2$, Ti—$SnO_2$, Co—$SnO_2$, Ni—$SnO_2$, Cu—$SnO_2$, Zn—$SnO_2$, Cd—$SnO_2$, Pt—$SnO_2$, $TiO_2$, $ZrO_2$, ZnO, MgO, CaO, $Li_2O$, $B_2O_3$, CO, $CO_2$, $SiO_2$, $GeO_2$, $N_2O$, NO, $N_2O_3$, $NO_2$, $N_2O5$, $SO_2$, $SO_3$, $SeO_2$, $SeO_3$, $TeO_2$, $TeO_3$, $Cl_2O$, $ClO_2$, $Cl_2O_7$, $Br_2O$, $BrO_2$, $I_2O_5$ and $I_2O_7$.

\* \* \* \* \*

UNITED STATES PATENT AND TRADEMARK OFFICE
CERTIFICATE OF CORRECTION

PATENT NO. : 7,155,959 B2 Page 1 of 1
APPLICATION NO. : 10/782720
DATED : January 2, 2007
INVENTOR(S) : Ming Su and Vinayak P. Dravid It is certified that error appears in the above-identified patent and that said Letters Patent is hereby corrected as shown below:

In the GOVERNMENT RIGHTS section, at Column 1, line 16, the Grant No. reading "F49620-02-1-0283" should be changed to --F49620-00-1-0283--.

Signed and Sealed this

Twentieth Day of March, 2007

JON W. DUDAS
*Director of the United States Patent and Trademark Office*